US006082364A

United States Patent [19]
Balian et al.

[11] Patent Number: 6,082,364
[45] Date of Patent: Jul. 4, 2000

[54] PLURIPOTENTIAL BONE MARROW CELL LINE AND METHODS OF USING THE SAME

[75] Inventors: Gary Balian; Gwo-Jaw Wang; David Diduch; Chang Hahn, all of Charlottesville, Va.

[73] Assignee: Musculoskeletal Development Enterprises, LLC, Charlottesville, Va.

[21] Appl. No.: 08/990,746

[22] Filed: Dec. 15, 1997

[51] Int. Cl.$^7$ ..................................................... A61B 19/00
[52] U.S. Cl. ..................... 128/898; 623/11.11; 623/16.11
[58] Field of Search ................................ 623/16, 11, 18, 623/66, 16.11, 11.11; 424/95; 530/838, 840; 514/2; 128/898

[56] References Cited

U.S. PATENT DOCUMENTS

| | | |
|---|---|---|
| 5,197,985 | 3/1993 | Caplan et al. . |
| 5,226,914 | 7/1993 | Caplan et al. . |
| 5,486,359 | 1/1996 | Caplan et al. . |
| 5,591,625 | 1/1997 | Gerson et al. . |
| 5,693,622 | 12/1997 | Wolff et al. ................................ 514/44 |
| 5,763,416 | 6/1998 | Bonadio et al. .......................... 514/44 |
| 5,785,965 | 7/1998 | Pratt et al. ............................ 424/93.21 |
| 5,837,283 | 11/1998 | McDonald et al. ...................... 424/450 |

OTHER PUBLICATIONS

M.J. Devine, et al., Bone Marrow Stem Cells Localize to Fractures in a Mouse Model, 43$^{RD}$ Annual Meeting, Orthopaedic Research Society, Feb. 9–13, 1997.

G.A. Dahir, et al., Preparation of a Cloned Osteogenic Bone Marrow Cell Line with a Traceable Genetic Market, 41$^{ST}$ Annual Meeting, Orthopaedic Research Society, Feb. 13–16, 1995.

Anderson, P., et al., "Cultures of a Cloned Bone Marrow Cell are Chondrogenic," 41$^{ST}$ Annual Meeting Ortho. Res. Soc. Trans., 20(2):462, Feb., 1995.

C.C. Su, et al. Bone Marrow Osteoprogenitor Cells Adhere to Titanium Implants, 42$^{ND}$ Annual Meeting, Orthopaedic Research Society, Feb. 19–22, 1996.

Q. Cui, et al., Steriod–Induced Expression of a Fat–Specific Gene by a Multipotentila Cell Cloned from Bone Marrow Stroma, 41$^{ST}$ Annual Meeting, Orthopaedic Research Society, Feb. 13–16, 1995.

Q. Cui, et al., A Transfected Osteoprogenitor Cell Beomces Adipocytic in Response to Steroids in Vitro and in vivo, 43$^{RD}$ Annual Meeting, Orthopaedic Research Society, Feb. 9–13, 1997.

R.E. Topping, et al., Effect of Factors Influencing Type X Collagen Expression in Periosteum, 41$^{ST}$ Annual Meeting, Orthopaedic Research Society, Feb. 13–16, 1995.

David R. Diduch, et al., Two Cell Lines from Bone Marrow that Differ in Terms of Collagen Synthesis, Osteogenic Characteristics, and Matrix Mineralization, The Journal of Bone and Joint Surgery, vol. 75–A, No. 1, pp. 92–105, Jan. 1993.

Q. Cui, et al., Steriod–Induced Adipogenesis in a Pluripotential Cell Line from Bone Marrow, The Journal of Bone and Joint Surgery, vol. 79–A, No. 7, pp. 1054–1063, Jul. 1997.

American Type Culture Collection, ATCC Designation CRL–12424, Nov. 7, 1997.

Su, C. C., Cui, Q., Wang, G. J., Surprenant, H. P., Collier, J. P., & Balian, G., "Bone Marrow Osteoprogenitor Cells Adhere to Titanium Implants," 42$^{nd}$ Annual Meeting, Orthopaedic Research Society, Feb. 19–22, 1996, p. 91–16.

Dahir G. A., Simon, Jr. C. G., Lillard T. S.,& Balian G. "Preparation of a Cloned Osteogenic Bone Marrow Cell Line with a Traceable Genetic Marker" 41$^{st}$ Annual Meeting, Orthopaedic Research Society, Feb. 13–16, p. 277.

Primary Examiner—Dinh X. Nguyen
Attorney, Agent, or Firm—Whitham, Curtis & Whitham

[57] ABSTRACT

Pluripotent stem-like cells obtained from bone marrow differentiate into osteocytes, chondrocytes and adipocytes, depending on the environment encountered and treatment. If systemically administered, the cells "home", that is migrate, to bone marrow. The cells may be transformed with recombinant DNA for the expression of both reporter genes, and biological factors, such as growth factors. The cells may be systemically administered to treat osteoporosis, osteolysis, improve bone implant adherence, augment bone growth or bone repair, augment cartilage repair, augment fat production for, e.g., breast augmentation, and the like.

14 Claims, No Drawings

PLURIPOTENTIAL BONE MARROW CELL LINE AND METHODS OF USING THE SAME

BACKGROUND OF THE INVENTION

Field of the Invention

This invention pertains to a pluripotential stem-like cell line obtained from mouse bone marrow stroma, cell line D1. These cells retain the ability to develop as osteocytes, chondrocytes and adipocytes, depending on environment and treatment. The cells are "homing" cells, that is, cells injected into the patient home to the bone marrow, unless specifically placed in another location, such as cartilaginous tissue or fat pouches and the like. This invention further pertains to transformed pluripotential stem cells carrying the genes for expression of one or more important exogenous proteins.

BACKGROUND OF THE PRIOR ART

In 1993, the inventors, and others, reported the recovery from mouse bone-marrow cells of a cell line which retained the potential to develop into an osteocyte, and exhibit osteogenesis, develop into a chondrocyte and engage in collagen synthesis, and develop as an adipocyte, with a consequential increase in lipid vesicles in the cell, these fat cell like properties being enhanced by treatment with steroids. The cell line was first described by Diduch et al., J. Bone and Joint Surgery, 75:92–105 (1993). The description of the isolation and recovery of bone cells set forth on pages 93–94 thereof is superficial, and not sufficient to enable one of skill in the art to recover either the D1 cell line, or similar pluripotential cells. In particular, the 1993 disclosure failed to teach those of skill in the art to separate adherent and non-adherent marrow cells. Only the non-adherent group included suitable progenitor cells. As detailed herein, these must be further fractionated and selected on the basis of their ability to proliferate without the need for monocyte colony stimulating factor. In the absence of the teaching to select out only non-adherent cells, and the use of monocyte colony stimulating growth factor, one of skill in the art would not have had a reasonable expectation of success in isolating a pluripotent, homing cell line such as the D1 cell line. The article itself notes that a second cell line, D2, did not express any of the osteogenic characteristics of its counterpart, and lacked the pluripotential of the D1 cell line. From its discovery, through the filing date of this patent application, control over the D1 cell line has been exercised exclusively by the inventors, and maintained at the University of Virginia's School of Medicine, at the Department of Orthopedics in Charlottesville, Va. Control over the cell line has been exercised by one of the co-inventors herein, Dr. Gary Balian. While repeated work discussing experiments employing the D1 cell line appeared in the literature in 1995 and 1996, none of this work describes the isolation of the D1 cell line, or indicates any source therefore.

Four separate presentations addressing this cell line were made at the 41$^{st}$ Annual Meeting, Orthopedic Research Society on Feb. 13–16, 1995, in Orlando, Fla. These presentations can be found in Ortho. Res. Soc. Trans. 20 (1995). Among the remarkable characteristics of the D1 cell line is its "homing" characteristic, that the D1 cell line, when injected (IV) into a mammalian host, "homed" or returned to the bone marrow. Thus, Dahir et al., Preparation of a Cloned Osteogenic Bone Marrow Cell Line With a Traceable Genetic Marker, page 277, demonstrated, through the introduction of a genetic marker into D1 cloned cells, that osteogenic cells from this line can successfully repopulate the marrow of host mice upon systemic injection. The bone marrow cells were effectively transfected and cloned with a gene for the expression of β-galactosidase, which had been previously used as a marker protein in other cells. Transfected cells were injected into the tail veins of mice. A determination of labeled cells demonstrated that the transfected D1 cells returned to the bone marrow in 31 of 32 cases. While a small percentage of labeled cells were found in lung tissue, no other examined tissues showed evidence of the labeled cells. The labeling was demonstrated to not affect alkaline phosphatase production and osteocalcin mRNA expression. The entirety of this disclosure is incorporated herein by reference.

Cui et al., at the same meeting, in Steroid-Induced Expression of a Fat-Specific Gene by a Multipotential Cell Cloned From Bone Marrow Stroma, page 564, demonstrated the pluripotential character of the D1 cell line by treating cells with a steroid, dexamethasone. In the face of steroid treatment, the number of lipid vesicles in the cells, and other fat cell characteristics, increased markedly. The number of adipocytic cells increased with time in the continuing presence of the steroid treatment. Cells that were not treated with steroids did not exhibit similar adipocytic characteristics. Thus, this cell line, which had been demonstrated to be osteogenic, was also demonstrated to be adipogenic, treatment with dexamethasone demonstrating enhanced fat cell like characteristics. As noted by Cui et al., when bone marrow cells become involved in the production of a fatty marrow, the bone becomes necrotic and weakens, rendering the bone susceptible to fracturing, particularly at the hip joint. This condition is particularly serious in the case of transplant patients who receive steroids to suppress organ rejection. The steroids stimulate adipogenesis by marrow cells, enhancing necrosis of the bone.

The third potential of this unique D1 cloned pluripotent cell type, development as a chondrocyte, enhancing the synthesis of cartilage and cartilage regeneration, is described by Topping et al., at the 41$^{st}$ Annual Meeting, page 29. There, it is noted that incubation of these cells in the presence of agarose elicits the expression of type II collagen and promotes chondrogenesis. It is further demonstrated that chondrogenesis is enhanced by the presence of insulin-like growth factor-1. Type X collagen is also produced by the hypertrophic chondrocytes of the callus in bone fracture healing. This was complimented by the presentation at the 41$^{st}$ Annual Meeting by Anderson et al., Cultures of a Cloned Bone Marrow Cell Are Chondorgenic, page 462, wherein the authors note that in addition to bone and fat production, the D1 cell line retains the ability to express a cartilage phenotype, reenforcing the observation that the D1 cell line is a pluripotential stem-like cell. Disappointingly, the report by Anderson et al., indicates the cartilage forming property of these cells is not accompanied by a complete dedication to the cartilage phenotype and is therefore likely to result in a fibrocartilaginous tissue which does not persist upon weight bearing but eventually degrades and is eroded.

In 1996, at the 42$^{nd}$ Annual Meeting, Orthopedic Research Society, Feb. 19–22 in Atlanta, Ga., Su et al., Bone Marrow Osteoprogenitor Cells Adhere to Titanium Implants, reported at Ortho. Res. Soc. Trans. 21 (1):91 (1996) reported that the D1 pluripotential or multipotential cells adhere to porous coated titanium rods both in vitro and in vivo. This vividly demonstrated, in vivo, the ability of the D1 cloned pluripotent cells to enhance implant penetration and attachment.

Present Work

Work on the D1 cell line has been ongoing throughout 1997. While this work does not constitute prior art with respect to the inventors, and the additional authors reflected in this work did not inventively contribute to the subject matter described in the reports beyond that contributed by the named inventors herein, significant advancement in the manipulation and use of the D1 cell line has been made.

At the 43$^{rd}$ Annual Meeting, Orthopedic Research Society, Feb. 9–13, 1997, Cui et al., A Transfected Osteoprogenitor Cell Becomes Adipocytic in Response to Steroids in vitro and in vivo, reported at Ortho. Res. Soc. Trans. 22 (1):138 (1997), the earlier work reported was extended, using β-gal marked bone cells. In vitro treatment with steroids (dexamethasone) demonstrated enhanced adipocytic production. In vivo experiments employed methyprednisolone as a steroid treatment. Mice, injected with the marked D1 bone marrow cells, and subjected to two weeks of steroid treatment, produced adipogenesis in the bone marrow and liver. Additionally in 1997, Devine et al., reported in Bone Stem Cells Localized to Fractures in a Mouse Model, Ortho. Res. Soc. Trans. 22 (2):330 (1997) confirmed the homing character of the D1 cell (employing transfected labeled cells). The experiment further demonstrated that IV injection of the bone cells lead to localization of the D1 cells within fracture hematoma and bone fracture callus. Systemic injection offers a superior method for introducing these cells, essential for fracture healing, as local injection of the cells into the fracture hematoma was met by tumorigenesis. Subsequently, in July, 1997, Cui et al., Steroid Induced Adipogenesis in a Pluripotential Cell Line from Bone Marrow, Journal of Bone and Joint Surgery 79:1054–1063 (1997), reported in detail, the differentiation of D1 cells into adipocytes in the presence of steroid (dexamethasone). Significantly, adipogenic changes were not found in D1 cells in the absence of the steroid. Expression of adipose-specific 422 (aP2) mRNA was also shown to increase markedly with increasing concentrations of steroid. Again, in untreated cells, this mRNA expression was not detectable. Treated cells showed a marked decrease in osteocalcin mRNA in D1 cells. Importantly, previously described pre-adipocyte cell lines, such as 3T3-L1 and 3T3-F422A, differentiate under normal culture conditions (no steroid) into lipid-containing cells. The D1 cell line is importantly distinguished as not developing adipocytic characteristics in the absence of steroids.

All of the above art comes from the joint inventors herein, Balian, Wang, Diduch and Chang. Other co-authors have contributed by participating in research directed by these co-inventors, or in the provision of the materials employed therein. The hallmark of the art collected to date is the failure to provide a repeatable, enabling method for isolation of a cell line of the differentiation and homing potential of the D1 cell line, which offers a wide variety of opportunities to treat multiple conditions, due to its ability to differentiate into an osteocyte, chondrocyte or adipocyte, depending on location and environment. Conditions ranging from improved bone implant adherence and bone fracture repair, bone regeneration and bone replacement due to osteoporosis, chondrogenesis and cartilage repair, as well as bone necrosis due to adipogenesis, and other conditions, could advantageously be impacted by selective treatment with homing, pluripotential bone marrow cells such as the D1 cell line. Accordingly, it remains an object of those of skill in the art to develop a reliable source for the D1 cell line or one like it, and methods of manipulation thereof, to permit treatment of the identified conditions.

SUMMARY OF THE INVENTION

The above objects, and others, are met for the first time by the provision of a deposit at the American Type Culture Collection, Rockville, Md., of the D1 cell line (D1 ORL UVA cell line). This deposit, made pursuant to Budapest Treaties, and as to which all restrictions will be removed upon the issuance of a patent on this application or any application claiming priority therefrom, can be accessed through accession number CRL-12424. The deposit was first made Oct. 28, 1997. The D1 cell line is also available from the University of Virginia School of Medicine, Orthopedic Research Laboratory.

A modified D1 cell may be employed in the enhancement of bone implant adherence or attachment, and fracture repair, by systemic injection. D1 cells home to the bone marrow of a mammal, and once located in the bone marrow, enhance osteocalcin expression. As noted, it appears that D1 bone cells, when systemically injected, locate preferentially in the fracture hematoma, and fracture callus, enhancing both the speed, and strength of bone fracture repair. These cells have been susceptible to transduction (transfection) with a variety of genes without impairing the ability of the D1 bone marrow cell to differentiate into an osteocyte. Transduction of the marrow cells with the gene encoding a polypeptide growth factor, which is itself involved in growth and repair of the skeleton, also improves adherence to porous coated metal implants, and improves fixation of hip and knee prosthesis. A suitable example of a plasmid for transduction comprises a 993 base pair (linear) sequence for murine IGF-1 available from Geneutech of California with either an osteocalcin or CMV promoter, as a Bluescript (pBS) plasmid. Similarly, transfection with insulin-like growth factor-1 provides for secretion of enhanced levels of IGF-1 directly to bone cells. The increased levels of growth factor combine with the enhanced bone marrow population aids the bone in growing into the prosthesis, and avoiding bone dissolution from the area surrounding the prosthesis. Similarly, the rate of repair of bone fractures, particularly in non-unions or mal-unions, is enhanced, reducing the term for immobilization and avoiding the need for surgical intervention or the stimulation of bone production for repair.

Due to the variable differentiation properties of the D1 cell line, chondrogenesis, and particularly, repair of cartilage at knee and elbow articulations, is enhanced by implanting D1 cells into defects within the surface of the cartilage. These cells are similarly advantageously transfected with IGF-1, which stimulates neighboring cells arising from the cartilage or from adjacent bone marrow, to differentiate into cartilage-producing cells. The continuous secretion of growth factor by the implanted cells, and the newly differentiated cells, gives rise to a cartilage matrix which retains its hyaline nature.

Adipogenesis, and bone necrosis, can be traced primarily to avascularization due to the production of a fatty marrow. Avascularization can be reversed by injecting D1 cells transfected with a gene for an angiogenic factor, such as vascular endothelial growth factor (VEGF) or other angiogenic factor. Suitable plasmids for transfiction include the muVGEF strain (base pairs 87–678 1 phase translation) with an appropriate promoter such as an osteocalcin or CMV promoter (Bluescript), the same were made available by Kevin Claffey of Boston, Mass. Others are generally available. In the alternative, differentiation into adipocytes may be advantageous in effecting or enhancing breast augmentation. Implanting D1 cells in fat pouches will, coupled with the administration of low level steroids, enhance the production of fat through cell division and adipogenesis arising from the implant itself, and by paracrine action of the implanted cells on local cell proliferation and increased fat production.

DETAILED DESCRIPTION OF THE INVENTION

This invention employs D1 bone marrow or stem-like cells or cells of similar type, which have unusual pluripotential characteristics in that, in the presence of the appropriate stimulus and location, the cells can differentiate into osteocytes, chondrocytes or adipocytes. These cells are available from the deposit CRL-12424, at the ATCC. The cells were obtained according to the following process, which differs sharply from that reported in Diduch et al.

Preparation of a Cloned Cell Line (D1) from Bone Marrow

Cells from bone marrow are obtained by washing out the marrow of a femur with DMEM and maintained in culture in a tissue culture flask at 37° C. for 24 hours. After 24 hours, the non-adherent cells are removed and centrifuged for 10 minutes. The adherent cells are discarded and the non-adherent cell pellet is suspended in pronase and incubated at 37° C. for 15 minutes. Horse serum is added to stop the reaction of the enzyme. The suspension of cells and serum is transferred and placed onto 15 ml of horse serum and centrifuged for 10 minutes. The horse serum is removed, and the cell clumps are disrupted with a pipette, transferred to a tissue culture flask and incubated for 48 hours at 37° C. The non-adherent cells are collected after 48 hours and treatment with pronase and centrifugation through horse serum steps are repeated. The horse serum is then removed and the cells are counted and placed in tissue culture flask. After 48 hours, the non-adherent cells are removed, centrifuged and washed with phosphate buffered saline. These non-adherent cells which contain the non-differentiated precursors of bone marrow stromal cells are maintained in culture in the presence of monocyte colony stimulating factor. The stromal population is separated from the hematopoietic cells by omitting colony stimulating factor from the additives in the culture medium. The non-adherent cells are thereby excluded from subsequent analysis and the adherent/stromal population is further maintained in culture without the addition of monocyte colony stimulating factor. Using cloning rings, individual cells were identified and isolated from neighboring cells, maintained until the colony reached a population of approximately 200 cells and the colony was transferred to an isolated tissue culture well. From this population of cells, sub clones were obtained by preparing serial dilutions in 24 chamber well plates, starting with approximately 1,000 cells per ml, each dilution being placed in a separate chamber well. Chambers that contained more than one cell or more than one focus of proliferation were not analyzed further.

The above-described D1 cell line was obtained from mouse bone marrow. The mouse bone marrow model is an excellent mimic and model for other mammalian systems, including the human system. There is a reasonable predictability that, following the methods described above, those of skill in the art will be able to secure pluripotential marrow cells from other mammalian donors, including humans. While it is believed that the D1 cell line, and other cell lines to be recovered, can be safely injected into heterologous hosts, including humans, without danger of rejection, this invention also contemplates the preparation of autologous cell lines for each mammalian host to be treated, or each individual, including human individuals. These cell lines may be used, in the same manner as the D1 cell line described above, in the therapy regimens described below. Actual in vivo examples of such therapy are confined to the mouse model, but are readily extrapolated to other mammalian individuals.

Skeletal Repair Therapy

The pluripotential marrow cells of this invention have been demonstrated to have a "homing" characteristic. That is, systemic injection of the D1 cell has been demonstrated to be followed by migration principally to the bone marrow, where the cells are capable of repopulating the bone marrow, and augmenting the process of bone deposit, outgrowth and repair. This is an important aspect of the invention, both because it permits systemic injection without tumorigenesis which is frequently associated with site-injection to the bone marrow or fracture site, and because it permits manipulation of the pluripotential marrow cells prior to injection. These features lend themselves to bone repair. Included within the scope of this aspect of the invention is improving the outgrowth into, and adhesion to, implants in bone, particularly surgical metal implants, such as hip prostheses and the like, as well as the augmentation of the bone repair process itself.

1. The D1 Cells Exhibit Bone Marrow Homing Properties

To demonstrate the homing nature of the D1 bone marrow cell line, D1 cells were selectively infected with a recombinant replication defective retrovirus providing a vector encoding β-galactosidase and neomycin-resistance. This infection or transfection was achieved without loss of osteogenic properties. The β-GAL marker made it possible to track the location of systemically injected D1 cells, in terms of the tissues where the transplanted cells are found.

Materials and Methods

Recombinant replication defective retrovirus was generated using the Ψ-CRE line producing replication-incompetent virus capable of infecting cells with a vector encoding β-galactosidase and neomycin-resistance. Danos et al., PNAS 85:6460–6464 (1988). Selection with G418 (neomycin) was carried out and subcloning by limiting dilutions performed to identify high producers of β-gal. Staining with xgal, a substrate for the enzyme, was used to identify cells that produce βgal. Studies were conducted to ensure that helper virus was not produced by the infected cell line which would in turn infect the cells in a host mouse. The osteogenic properties of wild-type cells, cells which had been infected and, infected and subcloned cells were examined by staining with von Kossa, determination of alkaline phosphatase activity, cAMP production in response to stimulation with parathyroid hormone, and hybridization of total RNA in Northern blots with osteocalcin cDNA. The response of the D1 cells and the infected D1 cells to acidic fibroblast growth factor (aFGF) was determined by incubation with 1 ng/ml aFGF in serum free medium. Total DNA in the cell layers was assayed using a spectrofluorometric method. Monolayer cultures of wild-type, infected, and infected and subcloned cells were lifted by mild mechanical agitation and $5 \times 10^6$ cells were injected into the tail veins of 4 week old Balb/c mice. The mice were sacrificed at 1, 3, 6 and 10 week intervals and tissue sections from bone, liver, lung, kidney, spleen, and muscle examined with xgal to determine the location of labeled cells. In addition, bone marrow cell cultures obtained from the mice that were injected with wild-type and transfected cells were examined histologically by staining with xgal. Quantitation of transfected cells was performed after incubation of cells in culture with fluorescein di-β-D-galactopyranoside (FDG) using fluorescence activated cell sorting (or flow cytometry) (FACS).

Results

Infection of D1 cells and subsequent selection with G418 and subcloning produced sixteen subclones, fourteen of which were positive for βgal by xgal staining. However, none of the subclones expressed alkaline phosphatase and therefore had lost the osteogenic phenotype. Infected cells which stained with xgal and were not selected from G418 retained their osteogenic properties which included staining with von Kossa, alkaline phosphatase activity and expression of osteocalcin mRNA. Both the D1 cells and the infected cells showed a two to three fold increase in total DNA when treated with aFGF indicating that infection did not alter the ability of the bone marrow cells to respond to the mitogenic activity of aFGF in vitro. No helper virus production was observed. Staining of tissue sections and bone marrow cell cultures from host mice that were injected with infected D1 cells revealed that the cells had returned to the bone marrow in thirty-one of thirty-two cases. Lung tissue also showed a small percentage of labeled cells. None of the other tissues that were examined showed evidence of cells that were labeled with xgal. Quantitation of infected cells by FACS demonstrated that between 30 and 40 percent were βgal positive. Bone marrow cells obtained from mice which were injected with infected cells were cultured in vitro and analyzed by FACS. Approximately 10 percent of the adherent cells were positive for βgal.

Discussion

The introduction of a genetic marker in an osteogenic bone marrow cell has been achieved successfully with the retention of the characteristic bone producing properties such as alkaline phosphatase production and osteocalcin mRNA expression. The traceable gene product, β-galactosidase, which has been used previously with myoblasts that were injected into muscle, Rando et al., JCB 125:12275–1287 (1994), was used in this study to demonstrate that osteogenic cells can successfully repopulate the marrow of host mice upon systemic injection.

2. D1 Bone Marrow Cells Adhere to Metal Implants

A phenomenon frequently encountered in patients receiving a metal implant, such as hip and knee prostheses, is osteolysis. This is a process wherein the bone surrounding the inserted prosthesis dissolves, resulting in loosening of the implant and possible need for further reconstructive surgery. Injected D1 cells can serve not only to repopulate the bone marrow at the site of the implant, but actually improve adherence to metal implants, which are typically provided with a porous coating. This permits better adherence to the implant, and ingrowth into the implant coating itself. This characteristic of the D1 cells is again demonstrated using cells transfected with a vector for β-galactosidase, which may also be referred to as D1-bag cells.

Materials and Methods

Porous coated titanium rods (DePuy, Inc.) were added to confluent monolayers of osteogenic cells, D1-bag, in culture. The rods were removed after 7 days, the adherent cells, and the cells released after treatment with trypsin were examined by staining with X-gal, the chromogenic substrate for β-galactosidase. In an in vivo experiment, porous coated titanium rods were implanted transversely into the distal femur of 31 adult Balb/c mice. Twenty-three of the mice each received $1 \times 10^6$ D1-bag cells by tail vein injection and 8 mice served as controls, without injection. The implants were removed at 2, 3, 4 and 8 weeks, cultured for 7 days and treated with trypsin to release the adherent cells. The cells that were released and the implants with cells that remained adherent after trypsin treatment, were maintained separately in culture for another 7 days. The surface of the rods and the cells that were released with trypsin were stained with X-gal, examined and microscopically compared with cells obtained from marrow blow-outs of the same animals. In some instances, the femurs were immersed in X-gal with the rods in situ, embedded in polymethylmethacrylate and sliced transversely through the rods. The sections were examined microscopically to locate D1-bag cells within the area of bone surrounding the titanium implant.

Results

D1-bag cells adhered to the surface of titanium rods in culture, were released with trypsin after 7 days in culture and retained their characteristic blue staining with X-gal. In the in vivo experiment, the bone marrow blow-outs from 74% of the mice contained D1-bag cells showed that these cells can repopulate the marrow of host mice, while D1-bag cells could be released with trypsin in 27% of the rods that were retrieved from the femurs. However, after trypsin treatment, D1-bag cells remained adherent to the surface of 54% of the rods. In sections that were examined histologically, D1-bag cells were localized to areas of bone adjacent to the titanium implant.

Discussion

This study demonstrates that multipotential cells from bone marrow stroma with osteogenic characteristics will adhere to porous coated titanium rods both in vitro and in vivo.

3. D1 Bone Marrow Cells Localized to Fractures

In addition to the homing properties of the D1 cell line, and its ability to repopulate bone marrow, and adhere to and improve ingrowth into metal implants, the D1 cell line importantly exhibits the characteristic that it localizes to the fracture site, particularly the fracture callus and hematoma, thus specifically enhancing bone repair. Again, the D1-bag cells, provided with the β-galactosidase marker, provides a convenient tool for confirming localization to fracture sites.

Methods

D1-bag cells were injected into the tail veins of twenty 8-week-old Balb/c mice (1 million cells per mouse) and, after femoral intramedullary rodding for stabilization, femur fractures were experimentally induced using a machine patterned on the Bonnarens-Einhorn apparatus. Bonnarens et al., J. Orthop. Res. 2:97–101 (1994). In twenty other mice, femur fractures were induced and an equal number of cells was immediately injected percutaneously into the fracture site. Control specimens for both injection methods received lactated Ringer's solution. At periods of 1, 2, 4, and 6 weeks after fracture, the mice were sacrificed and their femurs dissected for analysis. The callus tissue and marrow were stained with X-gal and examined histologically to detect cells which express β-galactosidase. Messenger RNA was prepared by extraction using Trizol. The number of transplanted D1-bag cells appearing in the callus was estimated by RT-PCR using primers for the neomycin resistance gene. This experimental protocol was approved by the Animal Research Committee at the University of Virginia Medical School.

Results

Localization of D1-bag cells within fracture hematoma and callus was noted in all tail-vein injected specimens at time points beyond 4 weeks post-injection. X-gal staining showed scattered distribution of injected D1-bag cells throughout the callus tissue, to an extent not seen in control specimens. Significant increases in mRNA expression were also observed in the calluses of D1-bag-injected mice compared to controls. Local injection of D1-bag cells into fractures showed no significant increase in localization compared to control specimens. Furthermore, tumor formation was seen after as little as 4 weeks where D1-bag was injected locally.

Discussion

Pluripotential bone marrow cells appear in fracture callus after systemic injection. Their time of detection (4 weeks after fracture) coincides with the repopulation of injected D1-bag cells in marrow. Although percutaneous local injection of the cells into actual fracture hematoma was expected to place identical numbers of stem cells where they could participate in bone repair, tumorigenesis appears to contraindicate it as a means of delivering osteogenic cells directly to the point of injury.

4. Transduction May Permit Delivery of Factors Stimulating Bone Repair

As noted above, the abilities to systemically inject D1 cells into a patient in need of skeletal repair, followed by homing of the bone marrow cells to the bone marrow, and in particular fracture sites and implants, permits manipulation of the marrow cells prior to injection. In particular, transduction of the marrow cells with a gene which encodes a growth factor involved in growth and repair of the skeleton, can help bone penetrate and grow into prostheses, increasing the rate of healing and fixation, while simultaneously preventing or delaying recovery from osteolysis. Fractured bones, particularly non-unions or mal-unions can be repaired at an accelerated rate using such transduced cells, and provide the opportunity to avoid or replace long-term immobilization with casts, and/or surgical intervention or electrical or ultrasound stimulation of bone production. Among the factors that may be advantageously introduced into the bone marrow cells of this invention are polypeptide growth factor such as VEGF and insulin-like growth factor-I. Again, to demonstrate the effectiveness in delivery of these "growth factor expression vehicles" directly to the bone marrow, and fracture point, D1-bag cells are employed.

Methods

D1-bag cells were also transfected with a cDNA encoding both insulin-like growth factor-I (IGF-I) together with a osteocalcin promoter and neomycin phosphotransferase. A suspension of $2 \times 10^6$ cells was transplanted into Balb/c mice by intravenous or intramedullary injection. A group of 32 mice was used to compare intravenous with intramedullary injection and analyzed over a period of 4 weeks. In a second group of 18 mice, a 1.2 mm drill bit was used to create a defect in the distal femur. The fate of the transplanted cells in the host mice was followed histologically by staining with X-gal. IGF-I was measured immunologically with Western slot blots of serum and marrow blow-outs. Neomycin phosphotransferase DNA was detected by PCR or DNA prepared from cells in the marrow blow-outs and from repair tissue in the cortical bone defects.

Results

Histologically, the transplanted cells which stained with x-gal appeared prominently in the marrow, adjacent to the calcified cartilage of the metaphysis and in the callus. Serum IGF-I levels increased gradually from 1 to 4 weeks in mice that had received the transfected cells. Neomycin phosphotransferase DNA appeared more prominently in host mice which received cells by intramedullary injection as opposed to intravenous injection. The amount of neomycin DNA increased initially after transplantation and diminished subsequently. The defects in animals which had received marrow cells by transplantation showed substantially more callus at 2 weeks in the cortical defects of animals which had received marrow cells by transplantation, and complete bone repair by 4 weeks, in contrast to the defects in control mice which had not healed by 4 weeks.

Discussion

The observations confirm that transplanted marrow cells localize to defects in bone. The results using transfected cells provide the opportunity to use mesenchymal cells to deliver genes of factors that enhance skeletal repair. The transplanted marrow cells and the products of the transfected genes alter the course of bone repair either directly by participating in the formation of repair tissue or by exerting a paracrine effect on the mesenchymal cells of the host.

Bone regeneration and skeletal repair addresses not only repair of fractures, and improved adherence and ingrowth in implants, but replacement of bone mass lost due to osteoporosis. This prevents fractures which are the consequence of weaker bones due to loss of bone mass, as well as replenishing calcium and phosphorous in the body, counteracting the excessive losses in bone which are experienced with aging in mammals, particularly women, post-menopausally, as well as the bone loss due to lack of physical activity associated with incapacity and senescence. Systemic injection of bone cells provides bone regeneration through two processes. The cells produce large molecules that constitute the extracellular matrix, and thus become involved in the production of connective tissue which is part of the bone. This extracellular matrix naturally becomes mineralized with calcium hydroxyapatite, and the transplanted cells become osteocytes which are embedded in the newly calcified (mineralized) matrix. Moreover, where bone marrow cells transduced with growth factors are employed, the delivery of growth factors to the hosts own bone cells by the transplanted cells stimulates the host cells, by paracrine effect, producing additional extracellular matrix which mineralizes, again adding to the bone mass of patients suffering from, or at risk of, osteoporosis. Thus, the first potential of the inventive marrow cells which are the subject of this invention, to provide by the deposited D1 bone marrow cells is the differentiation into osteocytes, with or without transduction. In the absence of transduction with growth factors, the osteocytes adhere to implants in bone, participate and accelerate the process of bone fracture repair, and become part of the repair tissue itself. This acceleration of skeletal repair can be further improved by transduction of the cells with genes encoding one or more growth factors, which further accelerates growth into and fixation of prostheses, suppresses osteolysis, accelerates the rate of repair of fractured bones, both through formation of additional osteocytes and an extended mineralization of extracellular matrix, and by stimulation of the host's own original bone cells, through paracrine effect.

Cartilage Repair

As noted, however, the bone marrow cells of this invention, typified by the D1 cell line, have other potentials. When implanted within the surface of cartilage, these bone marrow cells differentiate into chondrocytes, the activity of which in improving hyaline cartilage matrix production, can be further enhanced by transduction of the implanted cells with a growth factor, such as insulin-like growth factor-I (IGF-I). The production of type II collagen is important in avoiding the formation of cartilage repair with a fibrocartaliagionous tissue which degenerates as weight bearing of the joint involved progresses. The use of pluripotential bone marrow cells, such as the D1 cell line, will suppress, particularly when transduced with genes for growth factor such as IGF-I, the need for subsequent surgical treatment and/or joint replacement. Pluripotent cloned D1 cells also offer the potential for repair of both bone and cartilage (osteochondral) defects whereas chrondrocyte autotransplantation may repair only chondral defects.

Differentiation of the D1 cell line demonstrating the chondrogenic nature of these cells, was affected in vitro.

Materials and Methods

Cells from the mouse bone marrow cell line D1 were suspended in 0.5% low melt agarose and placed on a layer of 1% agarose to prevent adhesion of the cells to the tissue culture dish surface and subsequent spreading. Alternatively the cells were maintained in culture on a dish coated with poly(2-hydroxymethyl methacrylate) (poly-HEMA) in culture media containing 50 µg/ml sodium absorbate and 10% fetal bovine serum for periods between two days and three weeks. The media was removed and the cells were stained with Alcian blue. To prepare RNA for qualitative and quantitative analysis of gene expression, the cells were maintained in monolayers on non-coated tissue culture dishes for two days, in the presence of 1 mg/ml dextran sulfate. As a control, RNA was also prepared from cells that had been maintained on tissue culture dishes and allowed to adhere and spread without dextran sulfate. The media was removed, the cells were rinsed and total cellular RNA and poly $A^+$ RNA (mRNA) were prepared and analyzed by Northern blots, which were hybridized with type II and type I collagen cDNA. Type II collagen was also analyzed by competitive RT-PCR and quantitated using the NIH Quant software program.

Results

Both cells maintained in agarose or on poly-HEMA produced nodules which increased in size with time in culture. By three weeks, the majority of these cells were aggregated into large nodules which stained positively with Alcian blue. Analysis of total RNA showed that the cells that were maintained in agarose or on poly-HEMA expressed type II collagen mRNA. Analysis of Northern blots showed that a large proportion of type I collagen mRNA was produced by the same cells that express type II collagen. By contrast cells in monolayer culture that were attached and spread expressed primarily type I collagen and no type II collagen RNA. Analysis of poly $A^+$mRNA from cells treated with dextran sulfate produced type I and type II collagen mRNA. Quantitation of type II collagen RNA in the cells treated with dextran sulfate was performed by competitive RT-PCR and compared with RNA obtained from embryonic mouse leg. The D1 cells treated with dextran sulfate expressed approximately 25% of the amount of type II collagen RNA that was measured in mouse leg. The results indicate that the chondrogenic phenotype in the form of cartilage nodules and type II collagen mRNA expression can be achieved by these cells.

D1 Bone Marrow Cells Can Differentiate Into Adipocytes

Adipogenesis is the process by which pluripotent bone marrow cells, such as the D1 cells, can make fat and participate in the production of a fatty bone marrow. This is actually deleterious to the bone which becomes necrotic, and weakens as a result. Such bones are prone to fracturing, particularly at the hip joint. Transplant patients are particularly susceptible to bone necrosis, due to steroids administered to prevent organ rejection. It has been discovered that the steroids stimulate adipogenesis by bone marrow cells, leading to the production of a fatty marrow. Important evidence has been advanced, both in vitro and in vivo, which demonstrates that bone marrow cells become adipogenic in response to steroid administration. In the absence of steroid administration, adipogenesis ceases, or is dramatically reduced. Where steroid treatment is optional, patients at risk of bone necrosis and the factors complicated thereby should be carefully evaluated for alternate treatments. Where steroid administration is a requirement, bone marrow cells may be transplanted (systemically injected), which carry an angiogenic factor, such as vascular endothelial growth factor (VEGF). Since, as demonstrated above, the transplanted, transduced bone marrow cells return and populate the bone marrow, the expression at that point of VEGF or other angiogenesis agent, will restore vascularization, and prevent necrosis.

The response of D1-bag to steroids in vitro (dexamethasone) and in vivo (methylprednisolone) was evaluated.

Materials and Methods

The response of cells in culture to $1^{-7}M$ dexamethasone was determined. Cells were stained with both Sudan IV to determine adipocytic changes and with X-gal to localize β-gal. Total RNA extracted from these cells was analyzed on northern blots with 422(aP2) cDNA, a gene which is expressed specifically by fat cells, and with β-gal cDNA. Thirty-two eight-week-old Balb/c mice each received $1 \times 10^6$ D1-bag cells, either by tail vein injection (16 as Group A) or by direct injection into the marrow of the right distal femur (16 as Group B). Ten mice injected with saline served as controls (Group C). Ten of 16 mice in Groups A and B and 5 in Group C received methylprednisolone 3 mg/kg body weight per week by intramuscular injection. The mice were sacrificed at 1 week intervals and the distribution of D1-bag cells in tissue sections from bone, lung and liver was analyzed with an image analysis program.

Results

Treatment of cells in culture with dexamethasone produced an accumulation of lipid vesicles which stained with Sudan IV. Only D1-bag, and not the parent D1 cells (3), stained positively with X-gal. Hybridization of northern blots showed the expression of 422(aP2) mRNA. The expression of β-gal mRNA was observed only in D1-bag cells. Cells that were not treated with steroid did not express 422(aP2) mRNA. Tissue sections from animals in Groups A and B showed the appearance of D1-bag cells in lung and marrow but not in liver at 1 week. These cells persisted in bone marrow but disappeared from lungs after 1 week. In Group A (tail vein injected), approximately equal numbers of D1-bag cells were found in the left and right femurs. In Group B (marrow injected), the number of β-gal positive cells was approximately equal to that of Group A. Treatment with steroid for two weeks produced adipogenesis in bone marrow and liver. Some of the fat cells were β-gal positive, indicating that they originated from injected D1-bag cells.

As noted adipogenesis from the pluripotent bone marrow cells characterized by the D1 cell line poses significant health risks when it occurs in the bone marrow. Adipogenesis in other locations, however, may be highly desirable. Currently, breast augmentation is an invasive surgical procedure which requires implantation of foreign material into the hosts body. The massive lawsuits addressing certain breast implants bear witness to both the dangerous nature of this practice, and its wide popularity.

Pluripotent bone marrow cells, such as the D1 cell line of this invention, may be implanted directly into breast fat pouches. When stimulated by administration of steroids, these cells will increase the local production of fat and fat cells both through cell division and adipogenesis arising from implanted cells, and by paracrine action of the implanted cells on local cell proliferation and increased fat production. Thus, a process for breast augmentation, involving minimal invasive actions, and naturally occurring bone marrow cells, offers the opportunity for breast augmentation in conjunction with well developed steroid treatment regimens. While it is clear that the degree of augmentation will differ from individual to individual, all individuals should receive at least some benefit, due to the ability of these cells to differentiate into adipocytes, with augmented fat production.

This invention has been described generically, and by reference to specific embodiments. In vivo examples based on the mouse model are readily extrapolated to mammalian and human conditions. Methods of administration are systemic in nature, and preferably IV, for bone repair. Chondrogenesis, for enhanced cartilage growth and joint repair, as well as breast augmentation, is effective by local injection, to provide the proper environment for the desired differentiation. In this respect, injection into the cartilage mass, or fat pouches, for chondrogenesis and adipogenesis, respectively, do not raise the tumor generation problems exhibited by injection at or near a fracture site or bone marrow. Dosages will vary depending on the degree of augmentation desired, the individual, any factor or factors with which the cell has been transduced, such as growth factors, antigenic factors, and the like. Such variations, based on the in vivo and in vitro evidence set forth above, are within the level of skill of those in the art. Similarly, given the disclosure above, the selection of alternate cell lines, and sources of cell lines, is made possible. Such variations remain within the scope of the invention, unless expressly excluded by the recitation of the claims set forth below.

What is claimed is:

1. A method of augmenting bone growth in a mammal, comprising systemically administering a bone growth augmenting effective amount of a substantially purified preparation comprising a homogeneous population of cloned pluripotent bone marrow cells to said mammal, and allowing said cells to home to bone marrow of said mammal and thereafter differentiate into osteocytes which augment bone growth in said mammal.

2. The method of claim 1, wherein said systemic administration comprises intravenous administration.

3. A method of treating adipogenesis or bone necrosis in a mammal in need of said treatment, comprising administering to said mammal an effective amount of a homogeneous population of cloned pluripotent bone marrow cells, wherein the cloned pluripotent bone marrow cells are capable of differentiating into osteocytes, and homing to bone marrow, said cloned cells having been transformed by incorporation of a gene encoding an angiogenic factor, allowing said cloned cells to migrate to bone marrow of said mammal, and express said angiogenic factor.

4. The method of claim 3, wherein said angiogenic factor is VEGF.

5. A method of treating ostoeporosis or osteolysis, comprising administering an amount of a substantially purified preparation comprising a homogeneous population of cloned pluripotent bone marrow cells effective to enhance bone production by differentiation of said cells into osteocytes or stimulation of bone cells already present through paracrine effect or by both said differentiation and said stimulation.

6. The process of claim 5, wherein said pluripotent cells have been transformed with a gene for the expression of a polypeptide growth factor.

7. A method of repairing cartilage in a mammal exhibiting damaged cartilage, comprising implanting an amount of a substantially purified preparation comprising a homogeneous population of cloned pluripotent bone marrow cells effective to increase hyaline cartilage production in said mammal in said damaged cartilage through differentiation of said cells into chondrocytes.

8. The method of claim 7, wherein said implanted cells of said preparation have been transformed with a gene for expression of a growth factor.

9. A method of enhancing fat production in a mammal at a selected location, comprising implanting an amount of a substantially purified preparation comprising a homogeneous population of cloned pluripotent bone marrow cells at said selected location, and administering a pharmaceutically acceptable steroid to said mammal in an amount effective to differentiate the pluripotent cells of said preparation into adipocytes.

10. The method of claim 9, wherein said selected location is the breast of a mammal.

11. A method of augmenting repair of bone damage in a mammal, comprising administering an amount of a substantially purified preparation comprising a homogeneous population of cloned pluripotent bone marrow cells to said mammal, allowing said cells of said preparation to home to a site of said bone damage, and differentiate into osteocytes.

12. The method of claim 11, wherein said cells of said preparation have been transformed with a gene for expression of a polypeptide growth factor.

13. A method of producing a homogeneous population of cloned pluripotent bone marrow cells which have the ability to differentiate into osteocytes, and which, when introduced into a mammal systemically, lodge preferentially in bone marrow or callus of said mammal comprising:

(a) isolating non-adherent cells from a bone marrow sample;

(b) culturing the isolated non-adherent cells of (a) in a culture medium comprising monocyte colony stimulating factor;

(c) separating stromal cells from hematopoietic cells by omitting the monocyte colony stimulation factor from additives to the culture medium of (b);

(d) selecting those stromal cells of (c) which are adherent and able to proliferate in the absence of monocyte colony stimulation factor; and (e) forming clones from the cells produced in (d), wherein said cells have the ability to differentiate into osteocytes, and which, when introduced into a mammal systemically, lodge preferentially in bone marrow or callus of said mammal.

14. The method of claim 13, wherein the bone marrow is mouse bone marrow.

* * * * *